(12) United States Patent
DeLuca et al.

(10) Patent No.: US 7,763,599 B2
(45) Date of Patent: Jul. 27, 2010

(54) MODIFIED RETINOID COMPOUNDS AND THEIR USES

(75) Inventors: Hector F. DeLuca, Deerfield, WI (US); Margaret Clagett-Dame, Deerfield, WI (US); Sumithra Gowlugari, Fremont, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 98 days.

(21) Appl. No.: 12/061,247

(22) Filed: Apr. 2, 2008

(65) Prior Publication Data

US 2008/0194534 A1 Aug. 14, 2008

Related U.S. Application Data

(62) Division of application No. 10/758,767, filed on Jan. 16, 2004.

(60) Provisional application No. 60/440,683, filed on Jan. 17, 2003.

(51) Int. Cl.
*A61K 31/59* (2006.01)
*C07C 401/00* (2006.01)
(52) U.S. Cl. ..................... 514/167; 552/653
(58) Field of Classification Search .............. 514/167; 552/653
See application file for complete search history.

(56) References Cited

U.S. PATENT DOCUMENTS

| 3,984,544 | A | 10/1976 | Casmer et al. |
|---|---|---|---|
| 4,126,699 | A | 11/1978 | Gander et al. |
| 4,190,594 | A | 2/1980 | Gander et al. |
| 4,677,120 | A | 6/1987 | Parish et al. |
| 4,885,311 | A | 12/1989 | Parish et al. |
| 4,994,491 | A | 2/1991 | Purcell et al. |
| 5,049,584 | A | 9/1991 | Purcell et al. |
| 5,124,356 | A | 6/1992 | Purcell et al. |
| 5,837,728 | A | 11/1998 | Purcell |
| 7,126,017 | B2 | 10/2006 | DeLuca et al. |

FOREIGN PATENT DOCUMENTS

DE         2050658         5/1972

(Continued)

OTHER PUBLICATIONS

Bagley et al, "Fourier-Transform Infrared Difference Spectroscopy of Rhodopsin and Its Photoproducts at Low Temperature," Biochemistry, vol. 24, pp. 6055-6071, (1985).

(Continued)

*Primary Examiner*—Sabiha Qazi
(74) *Attorney, Agent, or Firm*—Andrus, Sceales, Starke & Sawall, LLP

(57) ABSTRACT

A method of minimizing or reducing the toxicity of a retinoid having a free carboxyl group and the resulting modified retinoids are described. The method comprises the step of esterifying the carboxyl group of the retinoid with a highly sterically hindered compound, which is preferably a secondary or tertiary alcohol. The resulting retinoid esters are rendered much less toxic than the starting or parent retinoid. This process provides a retinoid ester analog of reduced toxicity so that it may be administered orally with minimal side effects and with a much greater therapeutic window. The modified retinoid compounds are useful in the treatment and prophylaxis of all diseases and disorders where retinoid compounds have been shown effective.

26 Claims, 8 Drawing Sheets

Summary: Growth of Vitamin A-Deficient Rats

FOREIGN PATENT DOCUMENTS

| | | |
|---|---|---|
| EP | 0 337 689 | 10/1989 |
| WO | WO 92/12989 | 8/1992 |

OTHER PUBLICATIONS

Singh, "A Convenient and Improved Method for the Preparation of Retinoates," Synthetic Communications, vol. 12, pp. 447-451, (1982).

Singh, "Extrinsic Circular Dichroic Effects in Retinoates," Journal of the Chemical Society, Perkin Transactions 2, pp. 635-636, (1986).

Tsutsumi, "Positive-Type Resist Composition with Good Dry-Etching Resistance for Far Ultraviolet Ray and Manufacture of Semiconductor Integrated Circuit Using It," Chemical Abstracts, XP002285682, (1997).

Summary: Growth of Vitamin A-Deficient Rats

US 7,763,599 B2

MODIFIED RETINOID COMPOUNDS AND THEIR USES

CROSS-REFERENCE TO RELATED APPLICATION

This application is a divisional of U.S. patent application Ser. No. 10/758,767, filed Jan. 16, 2004, which claims priority to U.S. Provisional Application No. 60/440,683, filed on Jan. 17, 2003.

BACKGROUND OF THE INVENTION

The present invention is directed toward retinoids, and more particularly to a method of reducing the toxicity of retinoids and modified retinoids having reduced toxicity.

All trans-retinol, the major circulating form of vitamin A, is converted in the body to retinaldehyde and finally to all-trans-retinoic acid (atRA) (Blomhoff et al., 1992, Annu. Rev. Nutr. 12:37-57). atRA serves as the active form of vitamin A in cellular differentiation and growth, and embryonic development, whereas the aldehyde serves as the active form in the visual cycle (Palczewski and Saari, 1997, Curr. Opin. Neurobiol. 7:500-504). It is also believed that atRA serves as the active form in the reproductive functions of vitamin A (Clagett-Dame and DeLuca, 2002, Annu. Rev. Nutr. 22:347-381).

atRA, in addition to being a functionally active form of vitamin A, is also the parent of a family of drugs used both topically and orally for the treatment of a number of skin conditions (Ellis and Krach, 2001, J. Am. Acad. Dermatol. 45:S150-S157; Zouboulis, 2001, Skin Pharmacol. 14:303-315). Furthermore, it and some of its isomers are being considered as chemo-preventive agents, for example in epithelial tumors, and may also serve as a therapy for certain types of leukemias (Fenaux and Degos, 2000, Leukemia 14:1371-1377). atRA is believed to function by binding to a series of retinoic acid receptor subtypes, α, β and γ, that also vary in sequence due to differences in promoter usage and splicing (Chambon, 1996, FASEB J. 10:940-954). atRA and its analogs are believed to act through a nuclear receptor (RAR) to activate or suppress target genes responsible for its actions (Clagett-Dame and Plum, 1997, Crit. Rev. Euk. Gene Exp. 7:299-342; McCaffery and Dräger, 2000, Cytokine Growth Factor Rev. 11:233-249). atRA is formed in regulated quantities because it is extremely potent and readily activates the retinoic acid receptors (Duester, 2000, Eur. J. Biochem. 267:4315-4324). atRA is also rapidly metabolized so that its lifetime is relatively short (Roberts and DeLuca, 1967, Biochem. J. 102:600-605).

Because it is immediately active, pharmacological amounts of orally administered RA isomers have very serious side effects (Armstrong et al., 1994, in The Retinoids, pp. 545-572; DiGiovanna, 2001, J. Am. Acad. Dermatol. 45:S176-S182). Among them are frank toxicity resulting in weight loss, inanition, eye encrustation, and bone loss. Common side effects with pharmacological use of 13-cis RA (isotretinoin), a major orally administered form of RA, includes mucocutaneous toxicity and hyperlipidemia (Ellis and Krach, 2001, J. Am. Acad. Dermatol. 45:5150-5157). An even more serious problem is that RA isomers have significant teratogenic activity in pregnant mammals (Collins and Mao, 1999, Ann. Rev. Pharmacol. 39:399-430; Nau, 2001, J. Am. Acad. Dermatol. 45:S183-S187). These side effects have been a serious limitation to the use of oral retinoids in therapy. Although topically applied retinoids carry little teratogenic liability (Nau, 1993, Skin Pharmacol. 6:535-544; Buchan et al., 1994, J. Am. Acad. Dermatol. 30:428-434; Chen et al., 1997, J. Clin. Pharmacol. 37:279-284), there are other toxicities associated with this route of administration that limit their use including skin irritation (Orfanos et al., 1997, Drugs 53:358-388). A major reason for both oral and topical toxicity is that the retinoids are totally and immediately available upon administration. A process whereby a retinoid can be made available in vivo more slowly and more continuously would avoid peaks and valleys in the availability of the retinoid thereby providing an effective in vivo level of the compound over a more prolonged period of time and also avoiding or substantially reducing the toxicities that often result from the sudden availability of excessive amounts of the substance.

SUMMARY OF THE INVENTION

The present invention provides a method for modulating and regulating the in vivo activity of biologically active retinoid compounds, such as all-trans-retinoic acid. More specifically, this invention provides modified retinoid compounds that exhibit a desirable and highly advantageous pattern of biological activity in vivo, namely, the more gradual onset and more prolonged duration of activity relating to cell proliferation, cell differentiation and morphogenesis. As a consequence of such advantageous properties, these compounds exhibit minimal or at least substantially reduced toxicity as compared to the starting or parent retinoids and thus represent novel therapeutic agents that may be incorporated into a pharmaceutical composition containing a pharmaceutically acceptable excipient for the treatment and prophylaxis of all diseases and disorders where retinoid compounds have been shown effective, such as proliferative skin disorders characterized by abnormal cell proliferation or cell differentiation e.g. dermatitis, eczema, keratosis, acne and psoriasis. They should also be especially useful for the treatment of neoplastic diseases such as skin cancer, colon cancer, breast cancer, prostate cancer, lung cancer, ovarian cancer, neuroblastoma, and leukemia as well as for the treatment of skin conditions such as wrinkles, lack of adequate skin firmness, lack of adequate dermal hydration, and insufficient sebum secretion.

Structurally, the key feature of the modified retinoid compounds having these desirable biological attributes is that they are esterified with a highly sterically hindered compound, preferably an alcohol. Depending on various structural factors—e.g. the type, size, structural complexity—of the substituents on the attached alcohol, these derivatives are thought to modulate the biological action of the retinoid by hydrolyzing to the retinoid at different rates in vivo, thus providing for the "slow release" of the retinoid which results in a much greater therapeutic window for the biologically active retinoid in the body.

The in vivo activity profiles of such compounds can, of course, be further modulated by the use of mixtures of derivatives (e.g. mixtures of different retinoid ester derivatives) or the use of mixtures comprising one or more retinoid derivative together with one or more underivatized retinoid compounds or in combination with other biologically active compounds such as vitamin D compounds.

It is important to stress that the critical structural feature of the retinoid derivatives identified above is the presence of a highly sterically hindered group attached to the carboxyl group of the retinoid molecule. The presence of a highly sterically hindered group at that position imparts on the resulting derivatives the desirable slow release biological activity profile mentioned above. The fact that the introduction of a highly sterically hindered group at the free carboxyl group of the retinoid molecule markedly modulates the in vivo biological activity pattern of the resulting derivative was not appreciated previously. The realization of the importance of this specific modification, and the demonstration of its marked and highly beneficial biological effects form the basis of this invention.

Initially three sterically hindered alcohol esters of atRA were synthesized, namely, the t-butyrate ester (retinoyl t-butyrate, also referred to in this application as t-butyl-RA) as well as the pinacol ester (retinoyl pinacol) and the cholesterol ester (retinoyl cholesterol). The results of biological testing reveal that the t-butyrate ester is as active in vivo when given orally as is atRA. Yet when t-butyl-RA was given in large excess, it proved to be relatively non-toxic and, furthermore, a 10-fold higher dose of this compound compared to atRA was required to produce equivalent teratogenic effects. The pinacol ester appeared nearly as active as atRA in supporting growth of vitamin A-deficient rats compared to atRA. The toxicity of this compound was not tested but likely it also represents a very non-toxic form of atRA. The cholesterol ester was less effective in supporting the growth of vitamin D-deficient rats, but was till superior to vehicle in this activity.

Since almost all of the active ligand-specific retinoids have free carboxyl groups, esterifying them with a sterically hindered alcohol can be used to slow down the biological actions of the retinoids, thereby markedly reducing their toxicity at pharmaceutically acceptable doses and providing a much greater therapeutic window. The present invention thus provides a method whereby a retinoid can be rendered much less toxic, by derivatization with a highly sterically hindered compound, preferably an alcohol, so that the ester will be slowly hydrolyzed in the body to the retinoid. This would allow the retinoid derivative, i.e. the retinoid pro-drug, to be administered with much less danger of bone loss, weight loss, inanition, mucocutaneous irritation, hyperlipidemia and teratogenicity, which are side effects typically associated with oral retinoid use; or skin irritation as can occur with the use of topically applied retinoids.

DETAILED DESCRIPTION OF THE INVENTION

Figure 1:
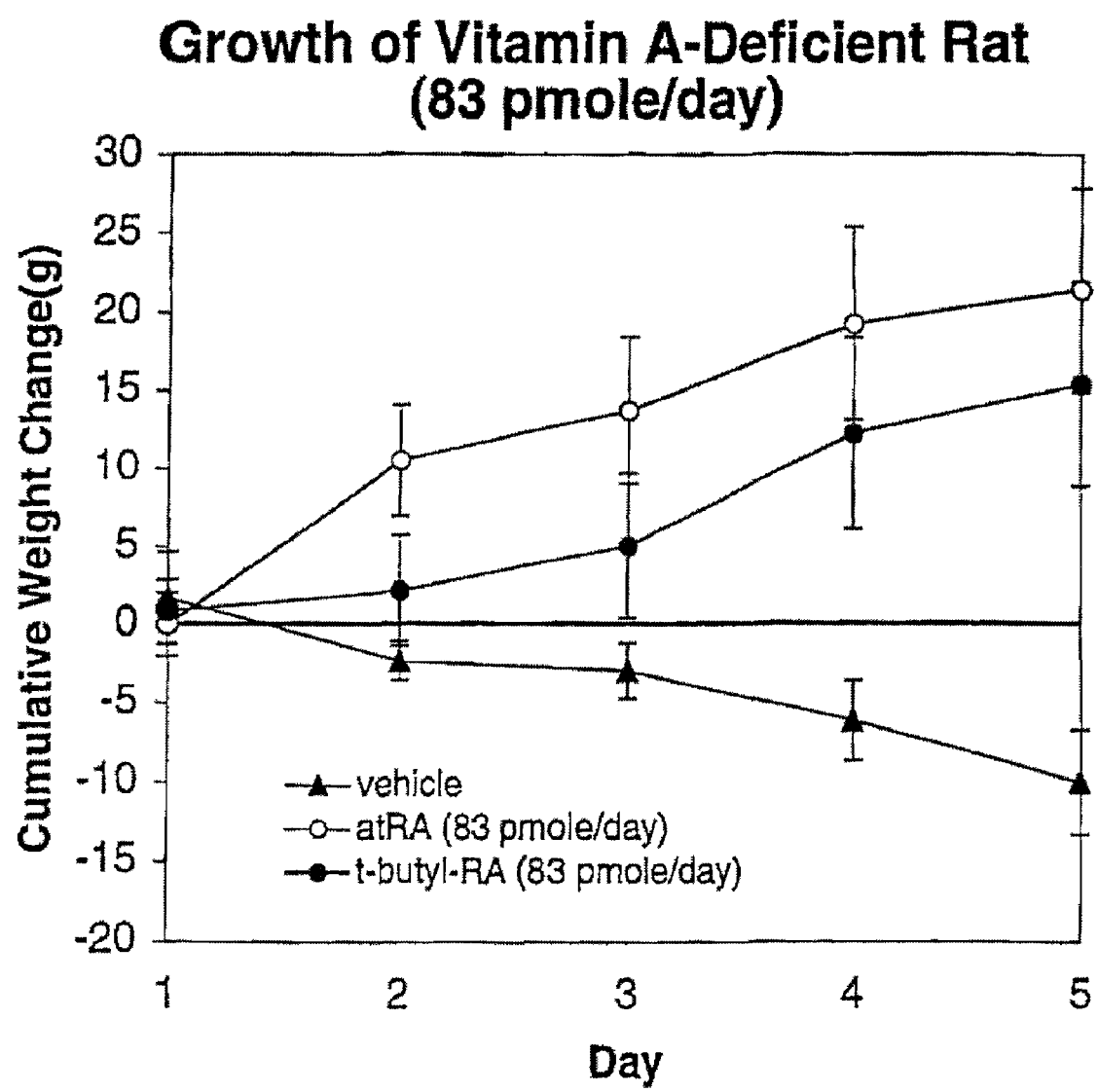
FIG. 1 is a graph illustrating growth of vitamin A-deficient rats given oil vehicle, or 83 pmole/day of either all-trans-retinoic acid (atRA) or t-butyl-retinoic acid (t-butyl-RA) for five days.

The present invention is directed toward a method of minimizing or reducing the toxicity of a retinoid having a free carboxyl group comprising the step of esterifying the carboxyl group with a highly sterically hindered compound, which is preferably an alcohol. The resulting retinoid esters are rendered much less toxic than the starting or parent retinoid. This process provides a retinoid ester analog of reduced toxicity so that it may be administered orally with minimal side effects and with a much greater therapeutic window.

Retinoic acid (RA) plays a fundamental role in cell proliferation, and cell differentiation and it may also prevent malignant transformation (Darmon, 1991, Sem. Dev. Biol. 2:219). The effects of RA and synthetic derivatives are mediated by two classes of nuclear receptors, the retinoic acid receptors (RARs) which belong to the erbA-related steroid/thyroid nuclear receptor superfamily and the retinoid X receptors (RXRs) which also belong to the same super family of steroid/thyroid hormones. Retinoids are analogs of vitamin A. Any of the synthetic retinoids that activate RARs and RXRs and have a free carboxyl group can be esterified in accordance with the present process to make them less toxic. In the present description, the term "retinoid" and/or "retinoid compound" refers to a class of compounds consisting of four isoprenoid units joined in a head-to-tail manner. All retinoids may be formally derived from a monocyclic parent compound containing five carbon-carbon double bonds and a functional group at the terminus of the acyclic portion. The term vitamin A should be used as the generic descriptor for retinoids exhibiting qualitatively the biological activity of retinol. This term should be used in derived terms such as vitamin A activity, vitamin A deficiency, vitamin A antagonist, etc. Examples of retinoids useful in the present process include 9-cis-retinoic acid, 11-cis-retinoic acid, 13-cis-retinoic acid, 9,13-di-cis-retinoic acid, benzoic acid-terminated retinoids and their heterocyclic analogs such as TTNPB, TTAB, Am80, Am580, SR11251, SR11247, CD666, CD367, chalcone-4-carboxylic acids, flavone-4'-carboxylic acids, etc. (Loeliger et al., 1980, Eur.J. Med. Chem.-Dhim. Ther. 15:9), (Kagechika et al., 1989, J. Med. Chem. 32:834), (Dawson et al. 1995, J. Med. Chem. 38:3368) illustrated below as well as

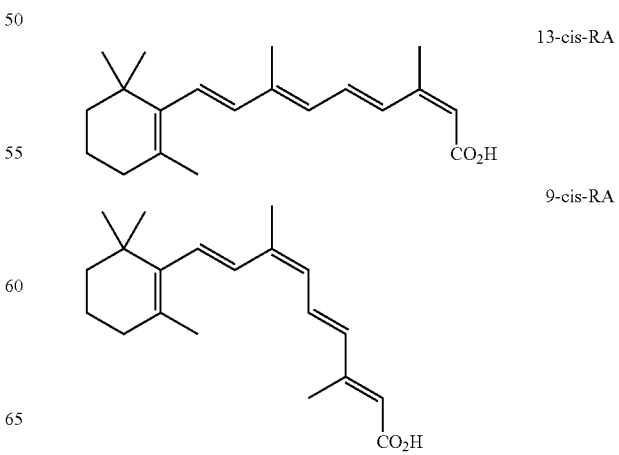

TTNPB
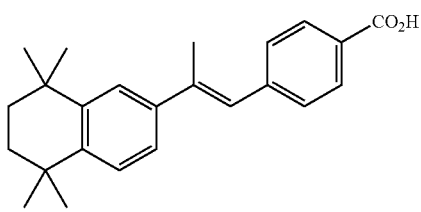

TTAB
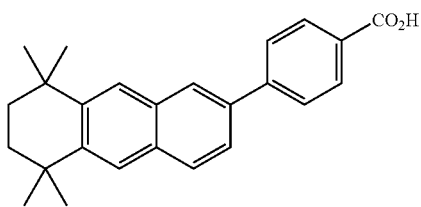

Am80
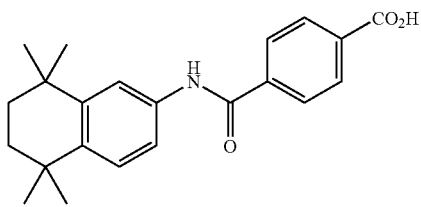

Am580
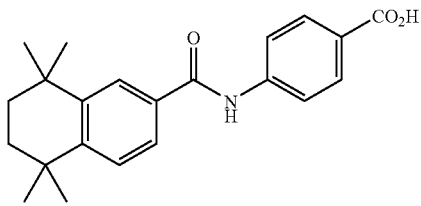

SR11251
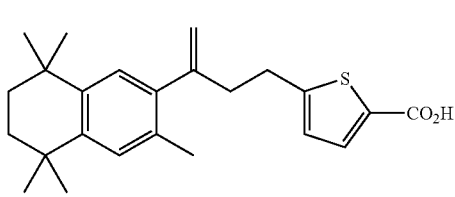

SR11247
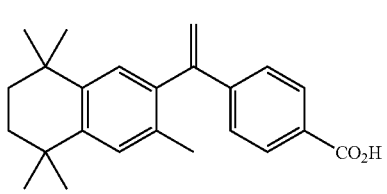

CD666
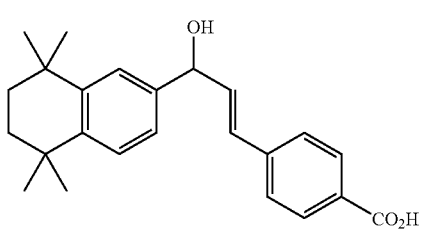

CD367
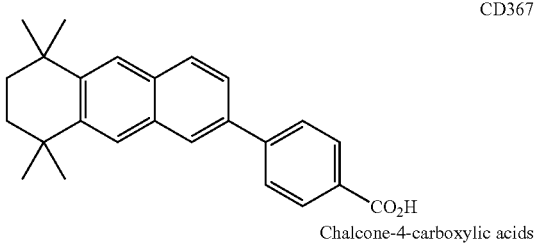

Chalcone-4-carboxylic acids
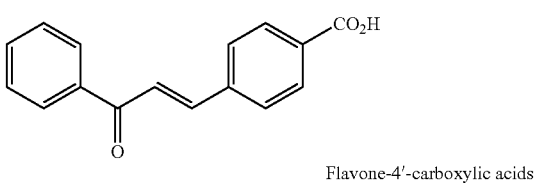

Flavone-4'-carboxylic acids
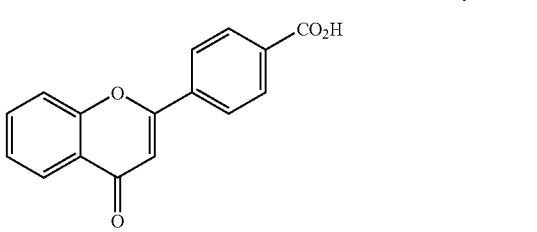

napthalenecarboxylic acid-terminatedated retinoids such as TTNN, CD437, CD417 or adapalene (Dawson et al., 1983, J. Med. Chem. 26:1653), (Dhar et al., 1999, J. Med. Chem. 42:3602) and many other carboxylic acid retinoids (AGN 190299 or tazarotenic acid and $R_o$ 10-9359 or acitretin).

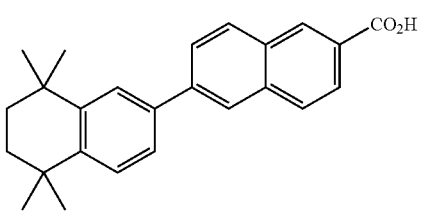

TTNN

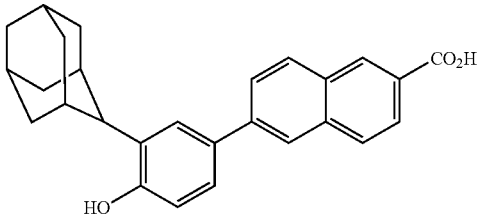

CD 437

Additional synthetic retinoids useful in the present method are described and illustrated below as well as in Dawson et al, "Synthetic Retinoids and their Usefulness In Biology and Medicine," Vitamin A and Retinoids, M. A. Livrea (ed.), pp, 161-196 (2000). See also: retinoids listed in http://www.chem.qmul.ac.uk/iupac/misc/ret.html as well as in Arch. Biochem. Biophys., 1983, 224, 728-731; Eur. J. Biochem., 1982, 129, 1-5; J. Biol. Chem., 1983, 258, 5329-5333; Pure Appl. Chem., 1983, 55, 721-726; Biochemical Nomenclature and Related Documents, 2nd edition, Portland Press, 1992, pages 247-251. The following list correlates the structures hereinafter shown with its name and/or code number.

| Retinoid | |
|---|---|
| Structure | Name/code number |
| 3-1 | trans-RA |
| 3-2 | 9-cis-RA |
| 3-3 | TTNPB/Ro13-7410 |
| 3-4 | UAB8 |
| 3-5 | CD367 |
| 3-6 | SR11365 |
| 3-7 | SR11256 |
| 3-8 | Am580 |
| 3-9 | Am80 |
| 3-10 | AGN 193836 |
| 3-11 | CD2019 |
| 3-12 | BMS188970 |
| 3-13 | Ro48-2249 |
| 3-14 | TTNN/SR3957 |
| 3-15 | BMS185282 |
| 3-16 | BMS185283 |
| 3-17 | BMS185354 |
| 3-18 | SR11254 |
| 3-19 | Ro44-4753 |
| 3-20 | CD437 |
| 3-21 | LGD100568 |
| 3-22 | SR11217 |
| 3-23 | LDG1069 |
| 3-24 | SR11246 |
| 3-25 | SR11345 |
| 3-26 | LDG100268 |
| 3-27 | AGN 191701 |
| 3-28 | AGN 192849 |
| 3-29 | HX600 |
| nr[6] | Ro25-7386 |

The highly sterically hindered alcohols useful in the present method comprise an alcohol selected from the group consisting of secondary alcohols and tertiary alcohols and mixtures thereof. In the present description, the term "secondary alcohol" refers to an alcohol having the formula

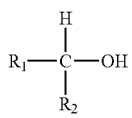

where $R_1$ and $R_2$, which may be the same or different, are each independently selected from the group consisting of an alkyl group which may be straight chain or branched in all isomeric forms having 1 to 20 carbon atoms, preferably 1 to 10 carbon atoms, and aryl. The term "aryl" in this description refers to a phenyl-, or an alkyl-, nitro- or halo-substituted phenyl group.

In the present description, the term "tertiary alcohol" refers to an alcohol having the formula

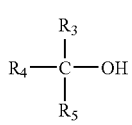

where $R_3$, $R_4$ and $R_5$ which may be the same or different are each independently selected from the group consisting of an alkyl group which may be straight chain or branched in all isomeric forms having 1 to 10 carbon atoms, preferably 1 to 5 carbon atoms, and an aryl group. The preferred tertiary alcohols are t-butyl alcohol, pinacol and cholesterol.

Synthesis

The preparation of retinoid ester compounds can be accomplished by a common general method, i.e. the conversion of the retinoid into its corresponding chloride or anhydride followed by reaction with the alcohol. The process represents an application of the convergent synthesis concept, which has been applied effectively for the preparation of various esters.

The overall process for the synthesis of the t-butyl ester is summarized by the SCHEMES 1-5.

Thus, to the all-trans-retinoic acid 1 in ether, was added N,N-dicyclohexylcarbodiimide, tert-butanol and catalytic amounts of dimethylaminopyridine and the reaction mixture was stirred for 24 h at room temperature to get the tert-butyl ester of retinoic acid (SCHEME 1). tert-Butyl ester of all-trans-retinoic acid 2 was also obtained from an intermediate acid chloride. The intermediate acid chloride could be obtained by the usage of oxalyl chloride or thionyl chloride. Thus, the retinoic acid is treated with equimolar quantities of oxalyl chloride at 0° C. to get the acid chloride and allowed to react in situ with equimolar amounts of pyridine and t-butyl alcohol at room temperature in dark for 4-5h SCHEME 2).

The ester can also be obtained by the reaction of all-trans-retinoic acid with carbonyldiimidazole to get the reactive imidazole which reacts with t-butyl alcohol to give the corresponding ester (SCHEME 3).

SCHEME 1

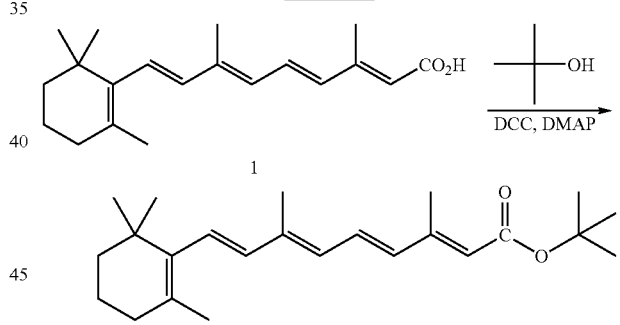

SCHEME 2

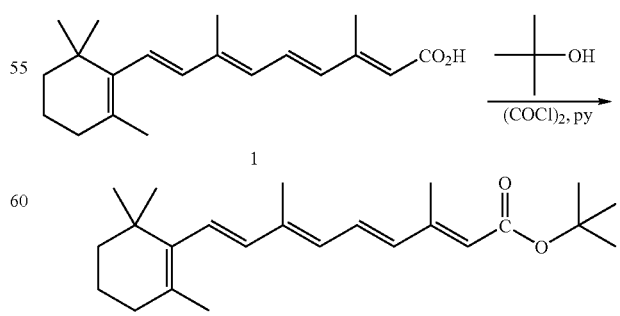

SCHEME 3

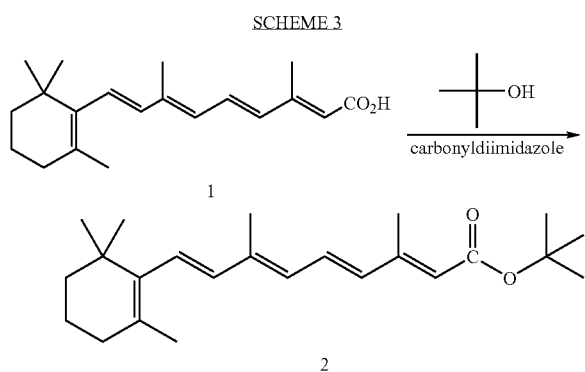

EXAMPLE 1

Scheme 2

Preparation of all-trans-retinoic acid tert-butyl ester 2: To a solution of all-trans retinoic acid (100 mg, 0.33 mmol) in anhydrous ether was added oxalyl chloride (42.3 mg, 0.333 mmol) at 0° C. and stirred at that temperature for 30 minutes and pyridine (28.7 mg, 0.363 mmol), 2-methyl-2-propanol (26.8 mg, 0.363 mmol) was added and stirred at room temperature in dark after which time the reaction was complete as indicated by the TLC. The reaction mixture was then quenched with water and extracted with ether (3×10 ml), saturated sodium bicarbonate solution (3×5 ml) and again with water (3×5 ml), dried ($MgSO_4$) and evaporated. The thick residue was redissolved in hexane and applied on silica Sep-Pak cartridge (2 g). Elution with hexane/ethyl acetate (9.7:0.3) provided the butyl ester of retinoic acid. Final purification was achieved by HPLC (10 mm×25 cm Zorbax-Sil column, 4 mL/min) using hexane/isopropanol (90:10) solvent system. Pure all-trans retinoyl butyrate 2 (98 mg, 82.6%) was eluted at $R_v$ 13 mL as a thick oil. $^1H$ NMR ($CDCl_3$): δ 1.034 (9H, s, t-Bu), 1.546 (3H, s, 20-$CH_3$), 1.719 (3H, s, 19-$CH_3$), 2.021 (6H, s, 16 & 17-$CH_3$), 2.405 (3H, s, 18-$CH_3$), 5.784 (1H, s, 14-H), 6.150 (1H, d, J=5.61 Hz, 7-H), 6.170 (1H, s, 10-H), 6.304 (1H, d, J=4.43 Hz, 12-H), 6.335 (1H, d, J=5.49 Hz, 8-H), 7.105 (1H, dd, J=11.48, 15 Hz, 11-H); MS m/z (relative intensity) 356 ($M^+$, 43), 342 (96), 328 (23), 300 (98).

EXAMPLE 2

Scheme 1

A solution of all-trans retinoic acid (100 mg, 0.33 mmol), N,N-dicyclohexylcarbodiimide (74.2 mg, 0.36 mmol), 2-methyl-2-propanol (26.68 mg, 0.36 mmol) and 4-dimethylaminopyridine (0.12 mg, 0.001 mmol) in anhydrous ether (5 ml) was stirred at room temperature in dark (protected from light) for 24 hours under argon. The N,N-dicyclohexyl urea formed was filtered and the filtrate washed with water (3×10 ml), 5% acetic acid solution (3×5 ml) and again with water (3×5 ml), dried ($MgSO_4$) and evaporated. The solid residue was redissolved in hexane and applied on silica Sep-Pak cartridge (2 g). Elution with hexane (10 ml) gave a small quantity of less polar compounds; further elution with hexane/ethyl acetate (9.7:0.3) provided the butyl ester of retinoic acid. Final purification was achieved by HPLC (10-mm×25 cm Zorbax-Sil column, 4 mL/min) using hexane/isopropanol (90:10) solvent system. Pure all-trans retinoyl butyrate 2 (22 mg, 18.5%) was eluted at R, 13 mL as a thick oil. $^1H$ NMR ($CDCl_3$): δ 1.034 (9H, s, t-Bu), 1.546 (3H, s, 20-$CH_3$), 1.719 (3H, s, 19-$CH_3$), 2.021 (6H, s, 16 & 17-$CH_3$), 2.405 (3H, s, 18-$CH_3$), 5.784 (1H, s, 14-H), 6.150 (1H, d, J=5.61 Hz, 7-H), 6.170 (1H, s, 10-H), 6.304 (1H, d, J=4.43 Hz, 12-H), 6.335 (1H, d, J=5.49 Hz, 8-H), 7.105 (1H, dd, J=11.48, 15 Hz, 11-H); MS m/z (relative intensity) 356 ($M^+$, 43), 342 (96), 328 (23), 300 (98).

EXAMPLE 3

Scheme 3

A solution of all-trans retinoic acid (100 mg, 0.33 mmol), carbonyldiimidazole (58.3 mg, 0.36 mmol) in anhydrous ether (5 ml) was stirred at room temperature in dark (protected from light) for 2 hours under argon. The imidazole formed was then reacted with 2-methyl-2-propanol (26.68 mg, 0.36 mmol) and stirred for 24 hours in dark at room temperature. The reaction mixture was washed with water (3×10 ml), 5% acetic acid solution (3×5 ml) and again with water (3×5 ml), dried ($MgSO_4$) and evaporated. The solid residue was redissolved in hexane and applied on silica Sep-Pak cartridge (2 g). Elution with hexane (10 ml) gave a small quantity of less polar compounds; further elution with hexane/ethyl acetate (9.7:0.3) provided the butyl ester of retinoic acid. Final purification was achieved by HPLC (10-mm×25 cm Zorbax-Sil column, 4 Ml/min) using hexane/isopropanol (90:10) solvent system. Pure all-trans retinoyl butyrate 2 (18 mg, 15.1%) was eluted at R, 13 Ml as a thick oil. $^1H$ NMR ($CDCl_3$: δ 1.034 (9H, s, t-Bu), 1.546 (3H, s, 20-$CH_3$), 1.719 (3H, s, 19-$CH_3$), 2.021 (6H, S, 16 & 17-$CH_3$), 2.405 (3H, s, 18-$CH_3$), 5.784 (1H, s, 14-H), 6.150 (1H, d, J=5.61 Hz, 7-H), 6.170 (1H, s, 10-H), 6.304 (1H, d, J=4.43 Hz, 12-H), 6.335 (1H, d, J=5.49 Hz, 8-H), 7.105 (1H, dd, J=11.48, 15 Hz, 11-H); MS m/z (relative intensity) 356 ($M^+$, 43), 342 (96), 328 (23), 300 (98).

EXAMPLE 4

(SCHEME 4)

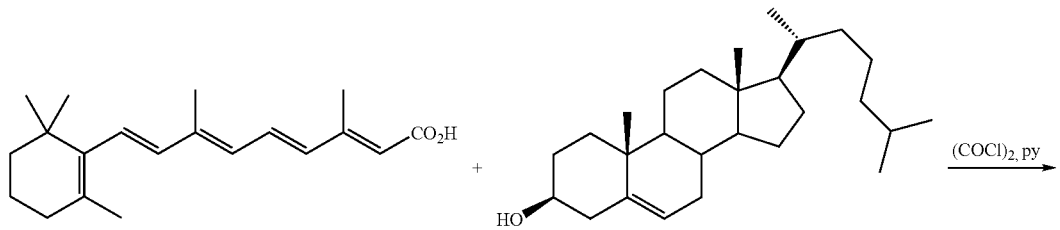

-continued

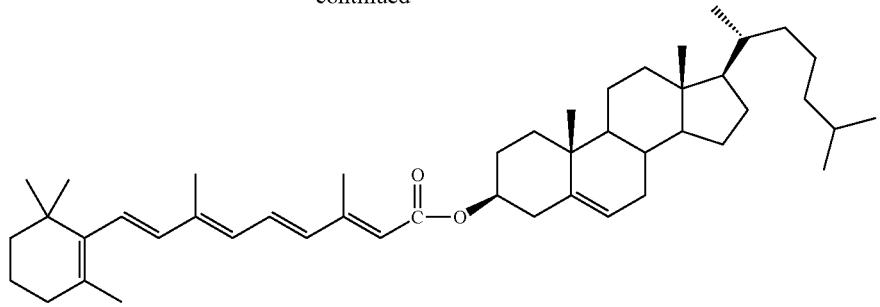

Preparation of all-trans-retinoic acid cholesterol ester (SCHEME 4): To a solution of all-trans retinoic acid (100 mg, 0.33 mmol) in anhydrous ether (10 Ml) was added oxalyl chloride (42.3 mg, 0.33 mmol) at 0° C. and stirred at that temperature for 30 minutes and pyridine (28.7 mg, 0.36 mmol) and cholesterol (140.36 mg, 0.36 mmol) were added and stirred at room temperature in dark for 16 h, after which time the reaction was complete as indicated by the TLC. The reaction mixture was then quenched with water and extracted with ether (3×10 Ml), washed with saturated aqueous NaCl solution, dried ($Na_2SO_4$) and evaporated. The thick residue was redissolved in hexane and applied on silica Sep-Pak cartridge (2 g). Elution with hexane/ethyl acetate (9.7:0.3) provided the cholesterol ester of retinoic acid. Final purification was achieved by HPLC (10 mm×25 cm Zorbax-Sil retinoic acid cholesterol ester (103 mg, 47%) was eluted at Rv 14 Ml as a thick oil. $^1H$ NMR ($CDCl_3$): δ 0.7 (3H, s, 18'-$CH_3$), 0.85 (6H, d, 26' & 27'-$CH_3$), 0.9 (3H, d, 21-$CH_3$), 1.546 (3H, s, 20-$CH_3$), 1.719 (3H, s, 19-$CH_3$), 2.021 (6H, s, 16 & 17-$CH_3$), 2.405 (3H, s, 18-$CH_3$), 4.625 (1H, m, 3'-H), 5.37 (1H, t, 6'-H), 5.78 (1H, s, 14-H), 6.150 (1H, d, J=5.59 Hz, 7-H), 6.17 (1H, s, 10-H), 6.30 (1H, d, J=4.4 Hz, 12-H), 6.335 (1H, d, J=5.5 Hz, 8-H), 7.10 (1H, dd, J=11.48, 15 Hz, 11-H); MS m/z 668, 369,300.

EXAMPLE 5

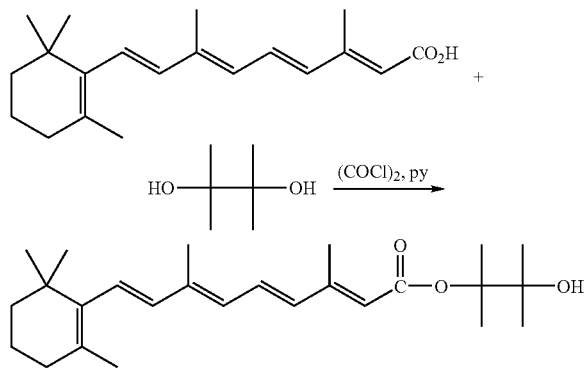

Preparation of all-trans-retinoic acid pinacol ester: To a solution of all-trans retinoic acid (100 mg, 0.33 mmol) in anhydrous ether (10 mL) was added oxalyl chloride (42.3 mg, 0.33 mmol) at 0° C. and stirred at that temperature for 30 minutes and pyridine (28.7 mg, 0.36 mmol) and pinacol (42.89 mg, 0.36 mmol) were added and stirred at room temperature in dark for 16 h, after which time the reaction was complete as indicated by the TLC. The reaction mixture was then quenched with water and extracted with ether (3×10 mL), washed and saturated aqueous NaCl solution, dried (Na2SO4) and evaporated. The thick residue was redissolved in hexane and applied on silica Sep-Pak cartridge (2 g). Elution with hexane/ethyl acetate (9.5:0.5) provided the pinacol ester of retinoic acid. Final purification was achieved by HPLC (10 mm×25 cm Zorbax-Sil column, 4 mL/min) using hexane/isopropanol (90:10) solvent system. Pure all-trans retinoic acid pinacol ester (103 mg, 47%) was eluted at Rv 16 mL as a thick oil. $^1H$ NMR ($CDCl_3$): δ 1.2 (6H, s, 2'-$CH_3$), 1.4 (6H, s, 1'-$CH_3$), 1.546 (3H, s, 20-$CH_3$), 1.719 (3H, s, 19-$CH_3$), 2.021 (6H, s, 16 & 17-$CH_3$), 2.405 (3H, s, 18-$CH_3$), 4.625 (1H, m, 1'-CH), 5.78 (1H, s, 14-H), 6.150 (1H, d, J=5.59 Hz, 7-H), 6.17 (1H, s, 10-H), 6.30 (1H, d, J=4.4 Hz, 12-H), 6.335 (1H, d, J=5.5 Hz, 8-H), 7.10 (1H, dd, J=11.48, 15 Hz, 11-H); MS m/z 400, 382, 300.

EXAMPLE 6 a. Experimental

The first test was to determine if the esterified compounds when given orally could restore normal growth of vitamin A-deficient rats. For this study, Sprague-Dawley, weanling rats were obtained from Harlan (Indianapolis, Ind.). They were fed the purified vitamin A-deficient diet previously described (Suda et al., 1970, J. Nutr. 100:1049-152) supplemented with vitamins D, E and K (White et al., 1998, Proc. Natl. Acad. Sci. USA 95:13459-13464). When the animals stopped growing and began to lose weight, they were administered the indicated doses per day dissolved in Wesson oil. Controls were given the Wesson oil alone (vehicle group). The weight change over the 5-day study period was analyzed by ANOVA, followed by a matrix of pairwise comparison probabilities using four post-hoc tests when the overall P value was less than 0.05. The post-hoc comparison tests included: Turkey HSD multiple comparisons, Sheffe test, Fisher's least-significant-difference test and the Bonferroni adjustment test. A result was considered significant only if more than two post-hoc analyses resulted in a P<0.05.

Figure 2:
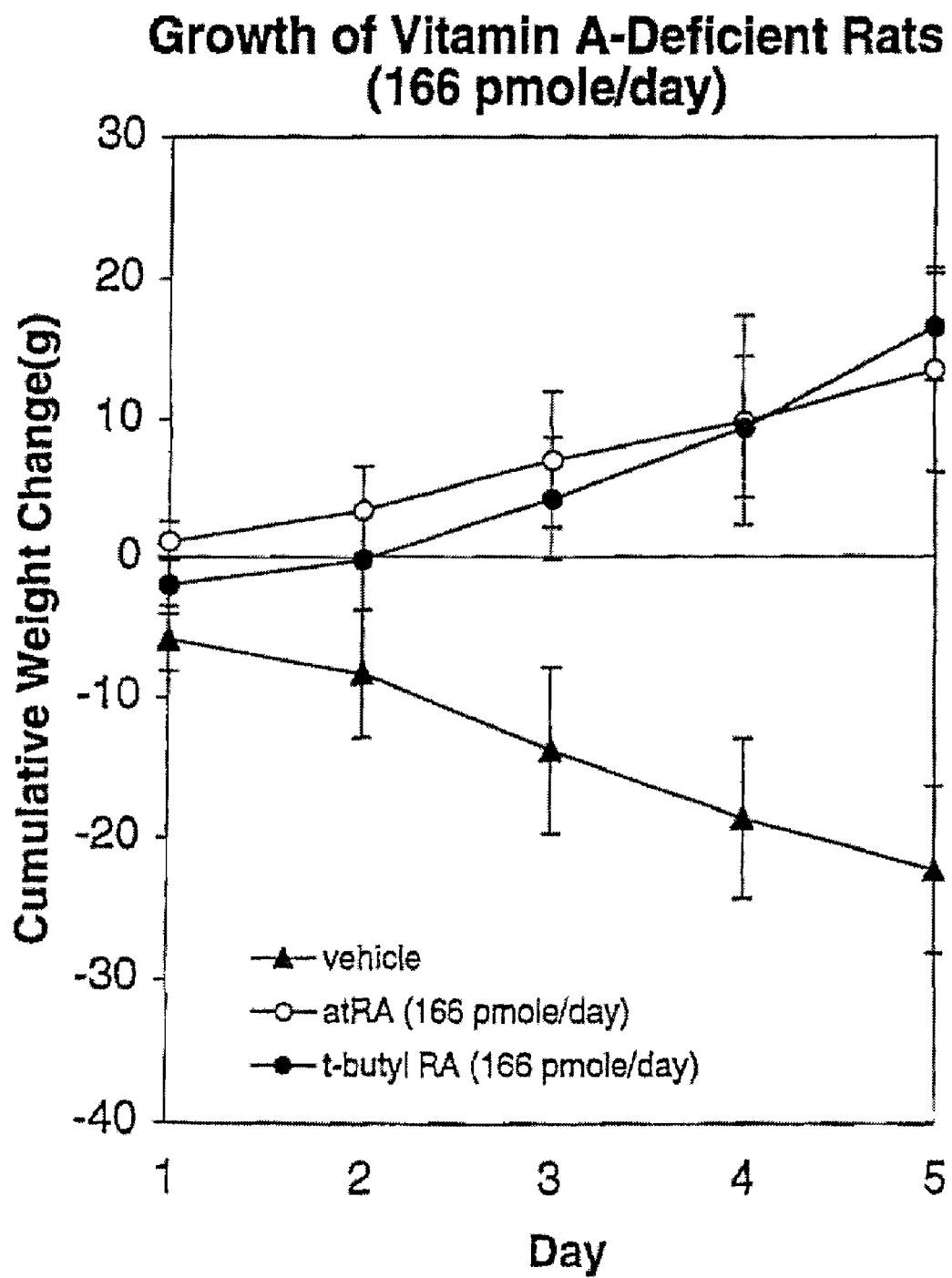
FIG. 2 is a graph illustrating growth of vitamin A-deficient rats given oil vehicle or 166 pmole/day of either all-trans-retinoic acid (atRA) or t-butyl-retinoic acid (t-butyl-RA) for five days.
Figure 3:
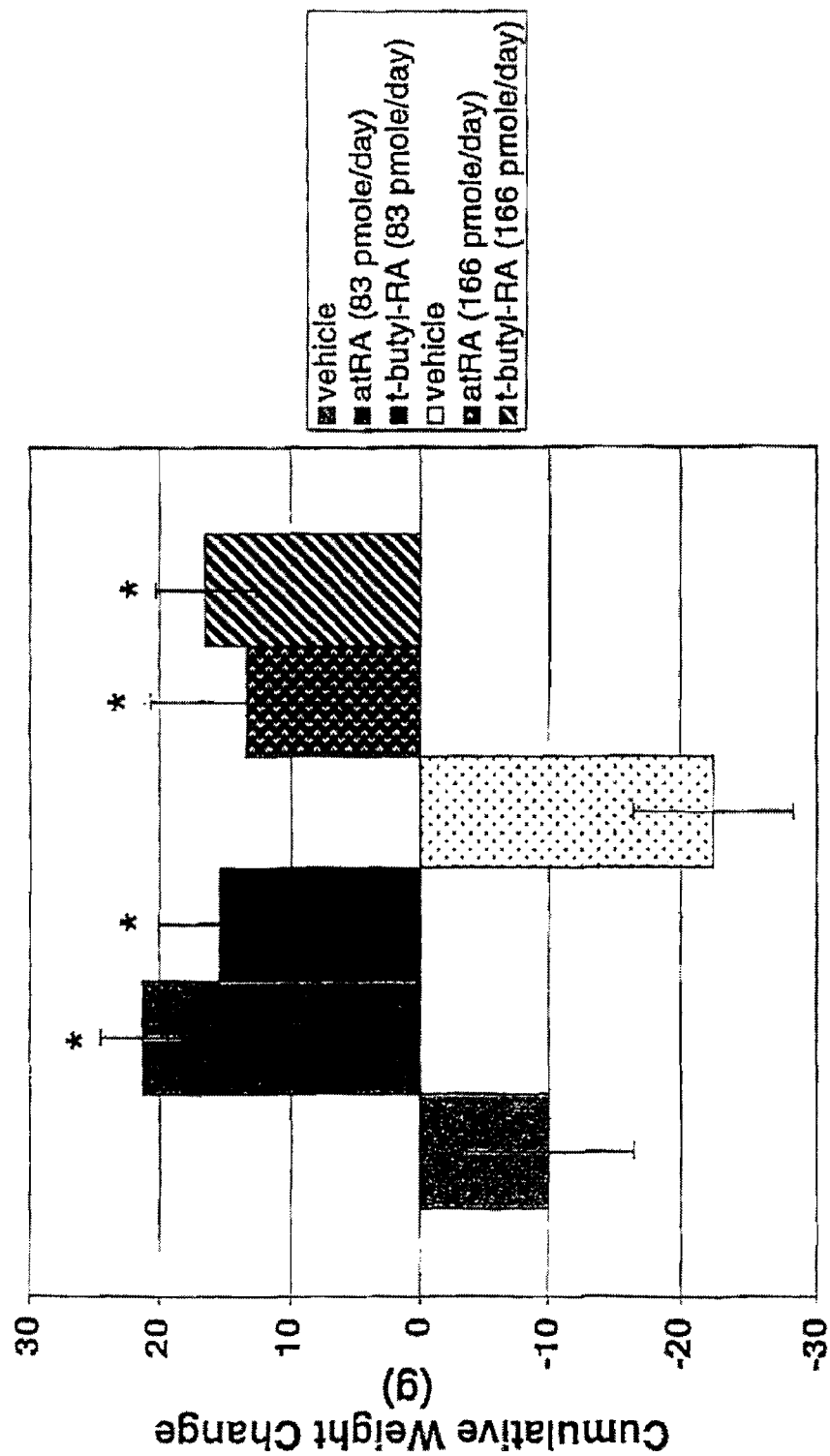
FIG. 3 is a bar graph summarizing the weight data illustrated in FIGS. 1 and 2.

The results of two experiments show that the t-butyl-RA derivative given at 83 pmoles/day (29.8 μg/day) supported growth over a 5-day period that did not differ significantly from that of the group fed an equal molar amount of atRA (25 μg/day). On the other hand, the animals receiving no vitamin A (vehicle control) continued to lose weight as indicated in FIG. 1 (P<0.01 compared to atRA and the t-butyl-RA groups). When the compounds were given at 166 pmoles/day for a 5-day period, (50 g/day atRA or 59.5 μg/day t-butyl- RA), the growth response of vitamin A-deficient rats was also equivalent, whereas, the vehicle-treated animals continued to lose weight (FIG. 2). FIG. 3 summarizes these results in a bar graph that illustrates that the t-butyl derivative is as active as atRA in vivo.

Figure 4:
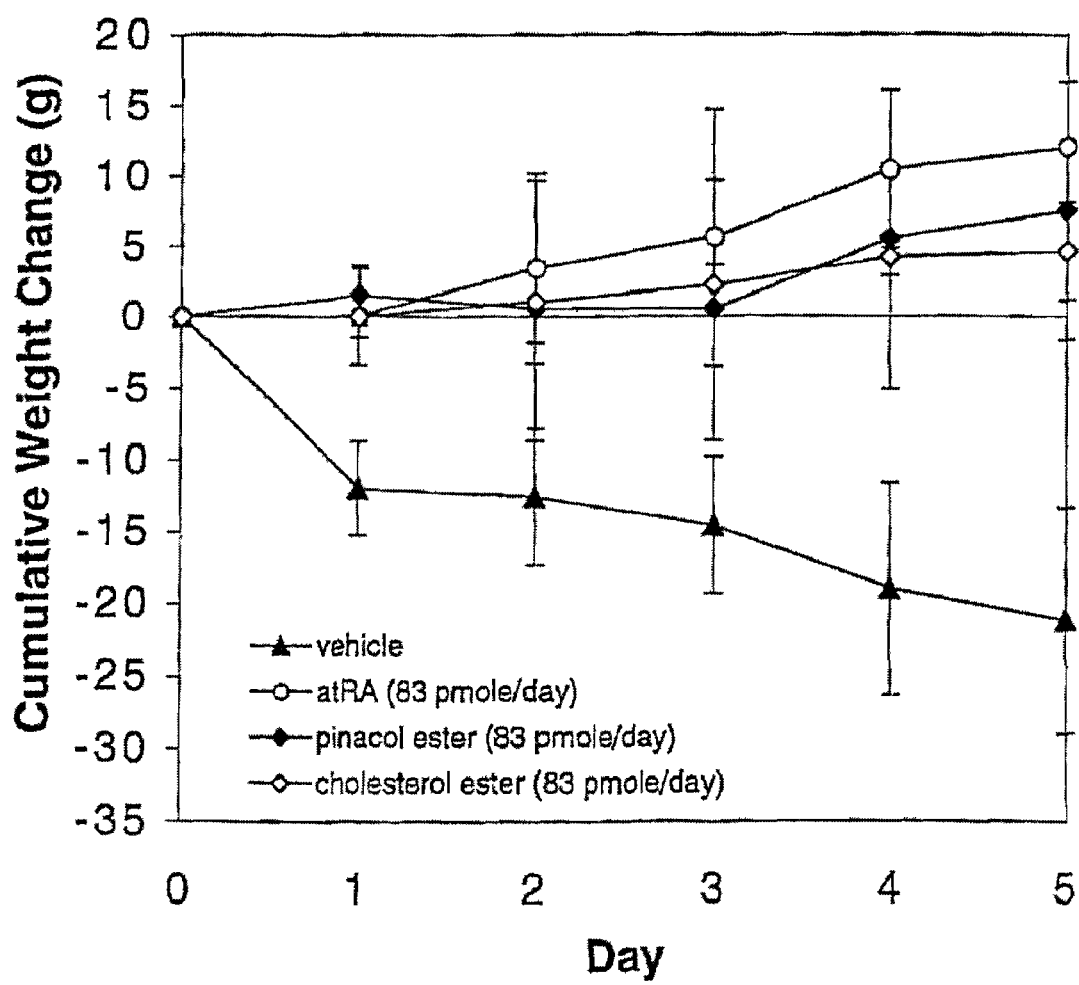
FIG. 4 is a graph illustrating growth of vitamin A-deficient rats given oil vehicle or 83 pmole/day of either all-trans-retinoic acid (atRA), the pinacol ester of atRA, or the cholesterol ester of atRA for five days.

FIG. 4 provides data obtained with the pinacol ester and the cholesterol ester. It shows that the pinacol ester has growth-supporting activity in vitamin A-deficient rats as does the cholesterol ester, and both compounds showed significantly enhanced growth compared to vehicle control animals (P<0.05). However, whereas the growth of atRA-supported animals was superior to that of the cholesterol ester-fed group (P<0.05), the pinacol ester was intermediary in efficacy between the two, and did not differ significantly from either of these two compounds. Thus, the pinacol ester is nearly equivalent to atRA in restoring the growth of vitamin A-deficient rats, whereas the cholesterol ester is less effective.

Figure 5:
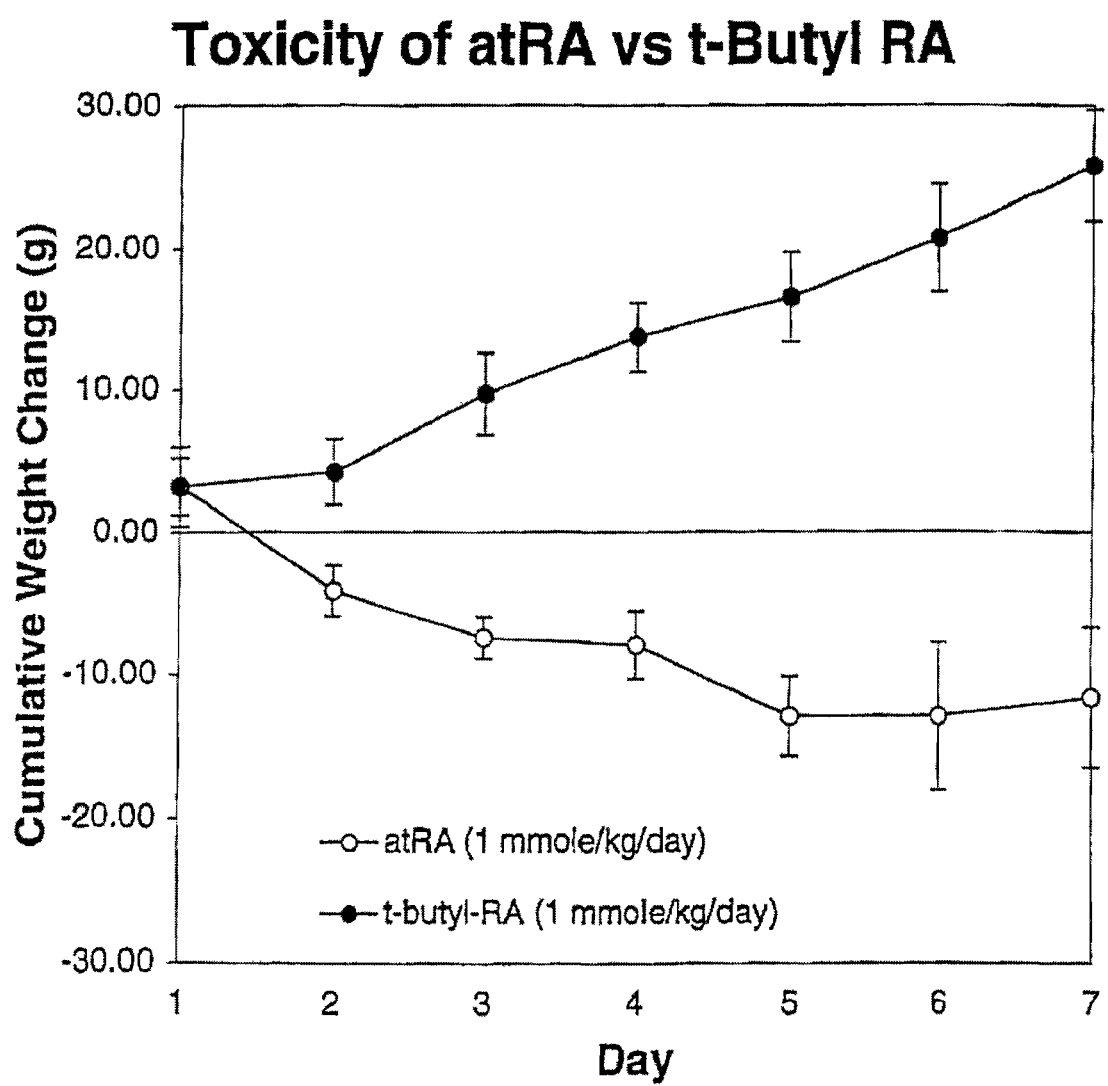
FIG. 5 is a graph illustrating the toxicity of all-trans-retinoic acid (atRA) versus t-butyl-retinoic acid (t-butyl-RA)
Figure 6:
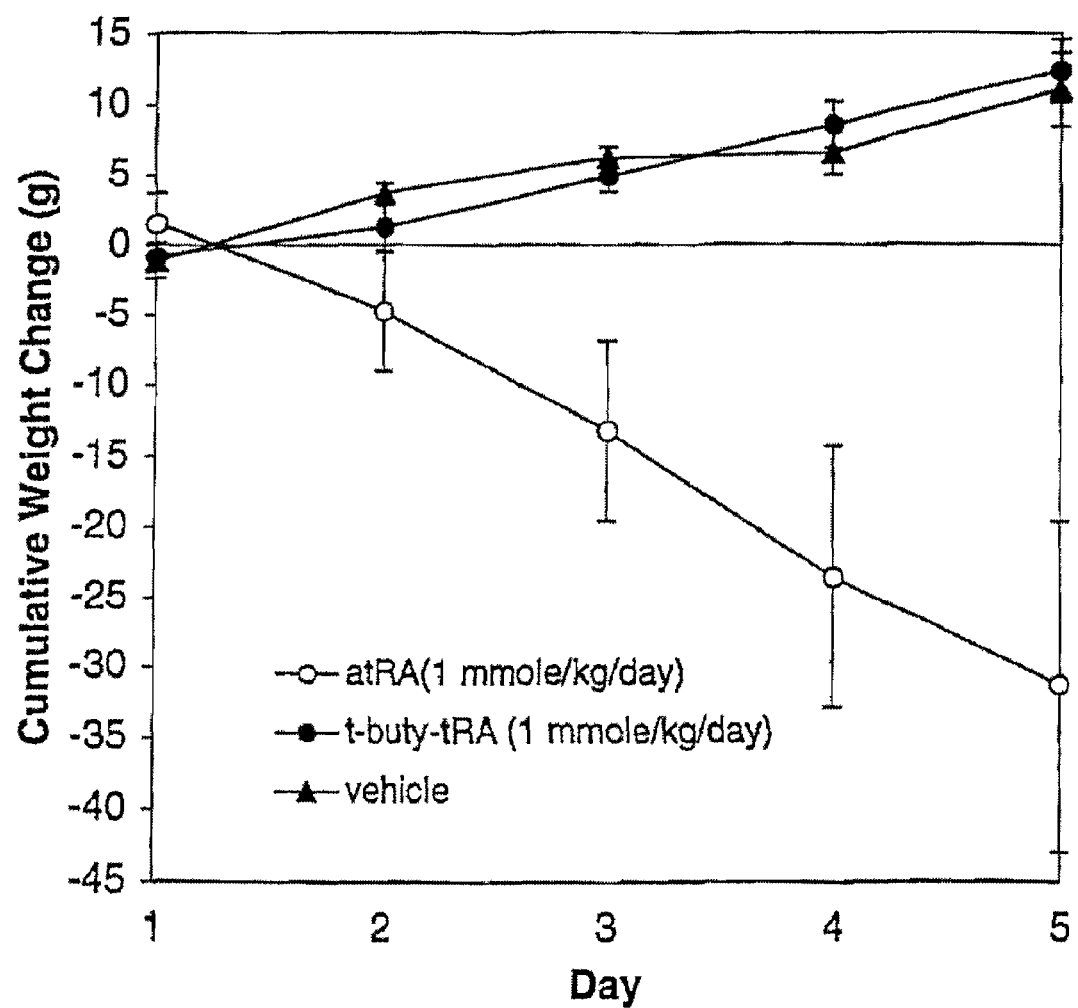
FIG. 6 is a graph similar to FIG. 5 illustrating the results of a second independent study of the toxicity of all-trans-retinoic acid (atRA) versus t-butyl-retinoic acid (t-butyl-RA); and an oil vehicle.
Figure 7:
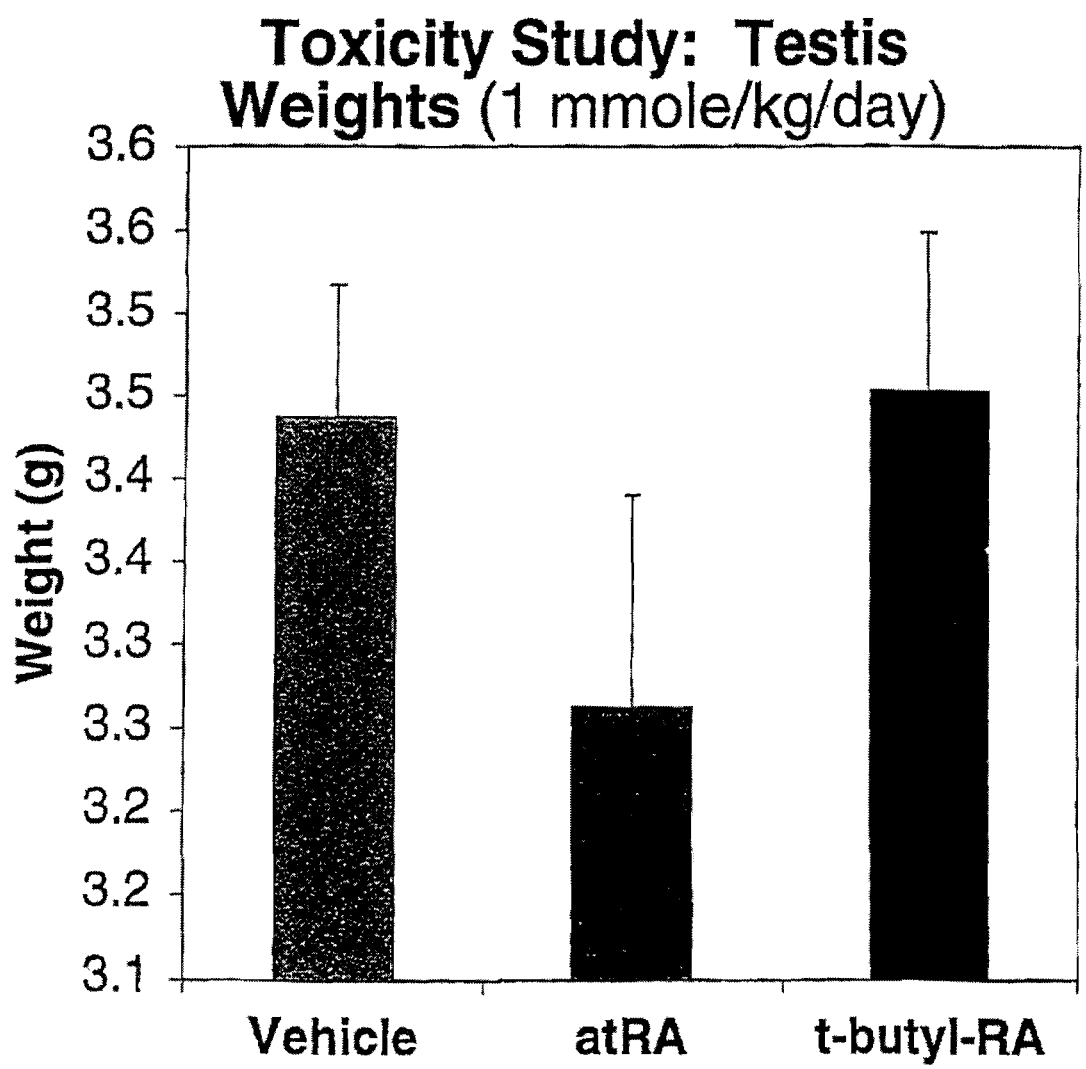
FIG. 7 is a bar graph showing the toxicity of all-trans-retinoic acid (atRA) as illustrated by the reduction in testes weight of the rats used to obtain the data of FIGS. 5 and 6.

Two independent toxicity studies were carried out with the t-butyl-RA derivative. FIG. 5 shows that 1 mmole/kg/day (300 mg/kg/day) of atRA produced severe acute weight loss over a period of 7 days as well as other signs of toxicity (loss of appetite, hair loss, diarrhea). In contrast, the same molar amount of t-butyl-RA (357 mg/kg/day) enabled continued growth of the animals and revealed no other externally obvious toxicity. In a separate study shown in FIG. 6, at equal molar concentrations (1 mmole/kg/day for 5 days), t-butyl-RA showed no apparent toxicity, whereas atRA produced severe acute weight loss (P<0.001) and outward symptoms of toxicity as described in the previous study. The toxicity of atRA was also illustrated by the reduction in testes weight that occurred in both experiments over the study period, whereas the t-butyl derivative showed no such indication (FIG. 7 and data not shown). However, the difference in testes weights between the atRA and t-butyl-RA groups was not statistically significant due to rather large biological variability.

Teratogenic activity of atRA is a serious drawback in its therapeutic potential. We, therefore, determined whether the t-butyl-RA derivative could circumvent the teratogenic activity exhibited by atRA. The results of the study are summarized in FIG. 8 and Table 1. A single dose of atRA (0.1 mmole/kg or 30 mg/kg) given to pregnant rats at embryonic day 12.3 produced significant shortening of the ulna (FIG. 8) and resulted in skeletal abnormalities in 13 embryos out of a total of 17 examined from four separate litters (Table 1). The control animals receiving the oil vehicle showed no abnormalities for the 18 embryos examined from four separate litters. The t-butyl retinoid given at 0.1 mmole/kg (35.7 mg/kg) also showed no abnormalities in 12 embryos examined from four litters. However, when a 10-fold higher dose of the t-butyl derivative (1 mmole/kg or 357 mg/kg) was given, 10 of 13 embryos showed abnormalities. The results of this experiment illustrate that atRA is, indeed, teratogenic and that the t-butyl derivative shares this liability, but only when given at a dose of 10 times higher than that of atRA. Thus, there is a larger window of safety when using the t-butyl-RA derivative when compared to atRA.

b. Biological Activity of the t-Butyl Ester or the Cholesterol Ester or the Pinacol Ester in Supporting Growth of Vitamin A-Deficient Rats.

Weanling male rats were obtained from the Harlan Company and were housed individually in hanging wire cages and fed the vitamin A-deficient diet described previously (Suda et al., 1970). At approximately 70 days of age, the animals began to show a leveling off of growth and began to show weight loss. At this time, they were used for the following studies: They were given either 0.1 ml of Wesson oil (vehicle) or the indicated dose of atRA dissolved in the vehicle or one of the derivatives at the indicated dose dissolved in the vehicle. Body weights were recorded daily and plotted as cumulative weight gain or loss over the study period as indicated on the graphs. A daily dose of 83 pmoles (25 µg/day) of atRA is near the minimum amount needed to produce normal growth in vitamin D-deficient rats as compared to the vehicle controls that continue to lose weight (FIG. 1). The t-butyl derivative at the same molar dose (83 pmoles or 29.75 µg/day) showed a growth response that did not differ from that of atRA over the 5 day test period, but was significantly different from the vehicle oil group (P<0.01). When the dose was increased to 50 µg/day of atRA or 59.5% g/day of the t-butyl derivative, as expected, the growth response was identical. Thus, t-butyl-RA is equal to atRA in potency and efficacy, and can fully satisfy the growth requirement for vitamin A-deficient rats. FIG. 3 provides a summary of these results.

FIG. 4 provides data obtained with the pinacol ester and the cholesterol ester. These results clearly show that both the pinacol ester and the cholesterol ester are able to support growth of vitamin A-deficient rats, with the pinacol nearly equivalent to atRA, and the cholesterol ester less so but nevertheless clearly much improved over the vehicle control. These results illustrate that these two esterified forms provide atRA to support growth. We estimate that the pinacol ester is nearly as active as atRA and the cholesterol ester is perhaps one-third as active.

c. Assessment of the Toxicity of atRA Versus the t-Butyl-RA Derivative.

We next examined the actute toxicity of the t-butyl derivative as compared to the atRA derivative in two independent trails. In these experiments, normal male rats weighing approximately 250-300 grams were used. They were individually housed in cages and given Purina lab chow as well as water ad libitum. In the first study shown in FIG. 5, a comparison between the t-butyl derivative and the atRA derivative illustrates that t-butyl-RA did not cause a weight loss when administered at 1 mmole/kg/day (357 mg/kg/day). This is an extremely large dose, and represents at least 3,600 times the amount of the t-butyl derivative needed to support a physiological growth response in vitamin A-deficient rats. On the other hand, an equal molar amount (300 mg/kg/day) of atRA produced a significant weight reduction (P<0.001) and symptoms of vitamin A toxicity. When the experiment was repeated, we again found that 300 mg/kg of atRA caused a severe weight loss compared to the t-butyl-RA and vehicle groups (FIG. 6, P≦0.001). On the other hand, the vehicle control and the t-butyl derivative given at 1 mmole/kg/day resulted in normal growth. Another indication of toxicity is testes weight as illustrated in FIG. 7. The testes weights of the vehicle and the t-butyl derivative were similar verifying that this ester did not cause overt toxicity, whereas a depression in testicular weight was observed with atRA given at 1 mmole/kg/day (300 mg/kg/day).

d. Teratogenic Activity of atRA Versus t-Butyl-RA.

Figure 8:
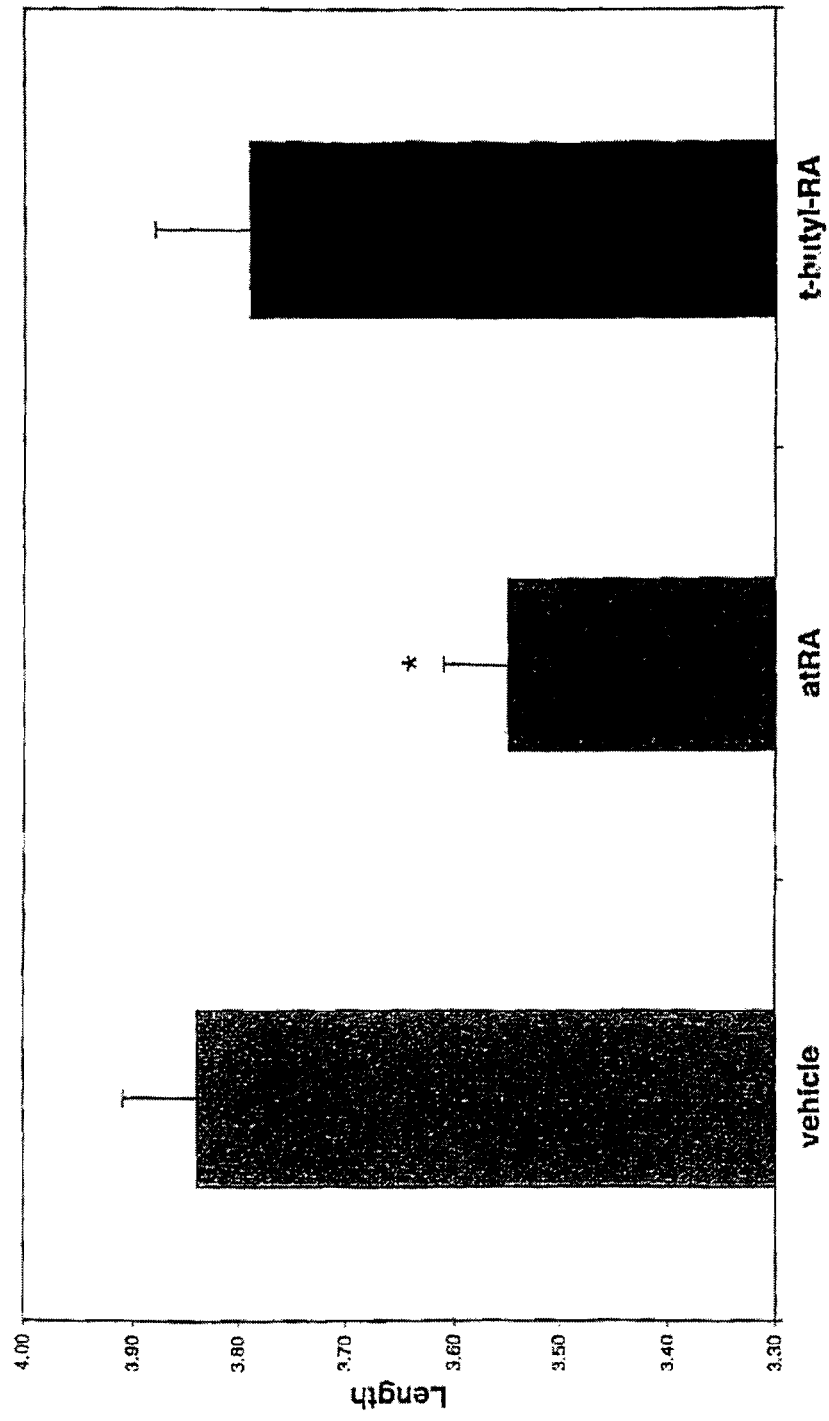
FIG. 8 is a bar graph illustrating the teratogenic activity exhibited by all-trans-retinoic acid (atRA) compared to the lack of toxicity of t-butyl-retinoic acid (t-butyl-RA) at 0.1 mmole/kg.

In this experiment, 19 female rats were obtained from Sprague Dawley and were individually housed in cages and given purina chow as well as water ad libitum. After approximately two weeks of acclimation to the animal facility, the females were placed with normal males on the same diet, between 6:00 and 9:00 pm. The following morning, the females were checked for vaginal plugs indicating fertilization. Vaginal smears were then checked for sperm and when shown to be positive, the pregnant rat was placed in the study. At embryonic day 12.3 between 9:00 and 10:00 in the morning, the rats received the following treatments given as a bolus dose in oil orally. Four groups of rats received the vehicle; four received 0.1 mmole/kg (30 mg/kg) atRA in the oil vehicle; another group received an equal molar amount (35.7 mg/kg) of t-butyl-RA; and a final group received a ten-fold higher dose (357 mg/kg) of t-butyl-RA. The embryos were removed by cesarean section on day 18.5 and weighed as well as checked for cleft palette. All embryos had approximately normal weight and no cleft palette was observed in any group. The embryos were fixed in 95% ethanol and a subset were randomly selected from each litter for staining to determine skeletal abnormalities. The only abnormalities observed at the 0.1 mmole/kg dose were markedly shortened ulnae in the atRA-treated group (FIG. 8). The results of this study show that t-butyl-RA is less teratogenic than atRA. The t-butyl-RA derivative is teratogenic when given at very high doses (1 mmole/kg), i.e. 10 times that of atRA (0.1 mmole/kg) where a similar percentage of skeletal abnormalities were observed (Table 1). We estimate, therefore, that the t-butyl derivative is approximately 10 times less teratogenic than atRA.

TABLE 1

Teratogenic activity of atRA and its t-butyrate ester

| TREATMENT | EMBRYOS abnormal/total examined |
|---|---|
| vehicle | 0/18 (0%) |
| atRA (0.1 mmole/kg) | 13/17 (76%) |
| t-butyl-RA (0.1 mmole/kg) | 0/12 (0%) |
| t-butyl-RA (1.0 mmole/kg) | 10/13 (77%) |

COMPOUNDS

The present invention also provides compounds which are useful in the treatment and prophylaxis of all diseases and disorders where retinoid compounds have been shown effective, such as proliferative skin disorders characterized by abnormal cell proliferation or cell differentiation (e.g. dermatitis, eczema, keratosis, acne and psoriasis) and they should provide especially useful for the treatment of neoplastic diseases such as skin cancer, colon cancer, breast cancer, prostate cancer, lung cancer, ovarian cancer, neuroblastoma, and leukemia as well as skin conditions such as wrinkles, lack of adequate skin firmness, lack of adequate dermal hydration, and insufficient sebum secretion.

These modified retinoid compounds are hydrolyzable in vivo to the parent retinoid, or analogs of the retinoid, over a period of time following administration, and as a consequence regulate the in vivo availability of the active retinoid, or analogs of the retinoid, thereby also modulating their activity profile in vivo. The term "activity profile" refers to the biological response over time of retinoid compounds such as atRA or analogs of atRA. Individual modified compounds, or mixtures of such compounds, can be administered to "fine tune" a desired time course of response.

As used herein the term "retinoid" or "retinoid compound" encompasses compounds which a class of compounds consisting of four isoprenoid units joined in a head-to-tail manner. All retinoids may be formally derived from a monocyclic parent compound containing five carbon-carbon double bonds and a functional group at the terminus of the acyclic portion. The term vitamin A should be used as the generic descriptor for retinoids exhibiting qualitatively the biological activity of retinol. This term should be used in derived terms such as vitamin A activity, vitamin A deficiency, vitamin A antagonist, etc. Examples of such retinoids were previously described and illustrated herein. As used herein the term "modified retinoid" or "modified retinoid compound" encompasses any retinoid in which one or more of the carboxyl functional groups present in such retinoid are modified to form an ester by derivatization with a highly sterically hindered compound, which is preferably an alcohol. A "highly sterically hindered compound" encompasses compounds which have groups of significant size that are immediately adjacent to the carbon atom containing the desired functional group, e.g. alcohol or amino, and provides a carboxyl-modifying group that can be hydrolyzed in vivo so as to regenerate the carboxyl function and the original parent retinoid.

Structurally, the modified retinoid compounds having the desirable in vivo bioactivity profile are ester derivatives of retinoids and may be represented by the formula

where R is a retinoyl and $R^1$ is a highly sterically hindered functional group selected from the group consisting of a first structure having the formula

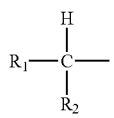

where $R_1$ and $R_2$ which may be the same or different, are each independently selected from the group consisting of a straight chain or branched alkyl group in all isomeric forms having 1 to 20 carbon atoms, preferably 1 to 10 carbon atoms, and aryl, and a second structure having the formula

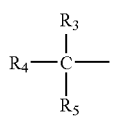

where $R_3$, $R_4$ and $R_5$ which may be the same or different are each independently selected from the group consisting of a straight chain or branched alkyl group in all isomeric forms having 1 to 10 carbon atoms, preferably 1 to 5 carbon atoms, and an aryl group.

The term "retinoyl" refers to a retinoid wherein the carboxyl functional group (—COOH) of the retinoid is missing its hydroxyl (—OH) group. Thus, a retinoyl can be represented by the formula

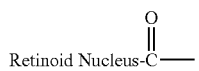

Accordingly, R in the above formula may be a retinoyl of any retinoid, and is preferably a retinoyl of a retinoid selected from the group consisting of
  all-trans-retinoic acid;
  9-cis-retinoic acid;
  11-cis-retinoic acid;
  13-cis-retinoic acid;
  9,13-di-cis-retinoic acid;
  TTNPB;
  TTNN;
  TTAB;
  UAB8;
  AM80;
  AM580;
  AM555S;

AGN 193836;
AGN 190299;
CD 2019;
CD 417;
$R_o$ 48-2249;
$R_o$ 44-4753;
$R_o$ 10-9359;
SR 11254;
BMS 185354;
AGN 190299;
CD 437 (AHPN);
SR 11247;
SR 11217;
SR 11237;
AGN 191701;
LDG 100268;
LDG 100568;
LGD 100754;
$R_o$ 25-7386;
BMS 188970;
SR 11004; and
SR 11203.

The preferred retinoyl is a retinoyl of all-tran-retinoic acid (atRA).

Any highly sterically hindered functional group or compound may be used as substituent $R^1$ as long as it hydrolyzes in vivo to the parent retinoid and reduces the toxicity of the retinoid.

Preferred highly sterically hindered functional groups comprise structures derived from secondary and tertiary alcohols such as tertiary butyl (t-butyl) having the formula

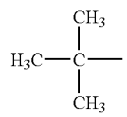

as well as pinacol having the formula

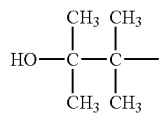

and cholesterol having the formula

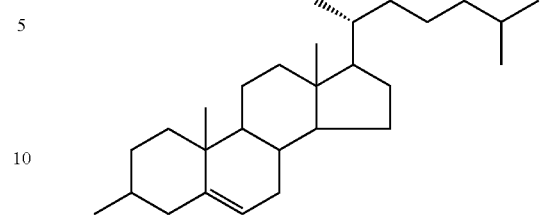

Three sterically hindered alcohol esters of atRA were synthesized as previously described herein, namely, the t-butyrate ester (retinoyl t-butyrate, also referred to herein as t-butyl-RA) having the formula

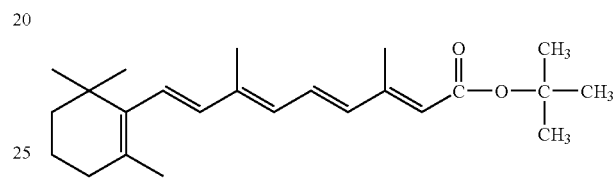

as well as the pinacol ester (retinoyl pinacol) having the formula

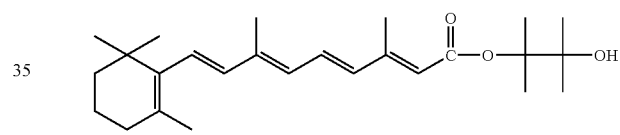

and the cholesterol ester (retinoyl cholesterol) having the formula

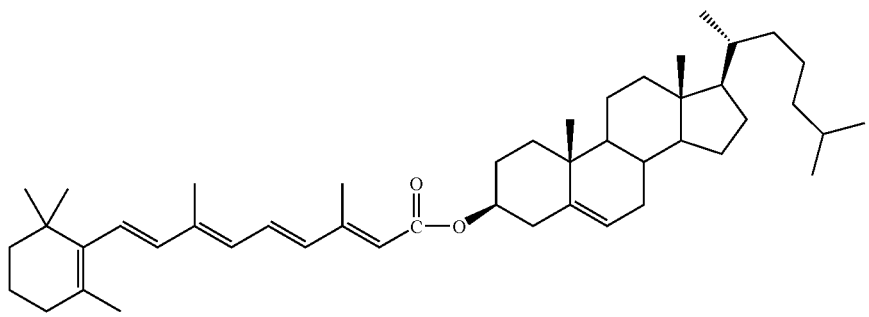

The above modified retinoid compounds may be administered to a subject in need thereof individually, in combinations of modified retinoid compounds, or in combination with other active pharmaceutical agents, together with a pharmaceutically acceptable excipient, in a pharmaceutical composition. As is well known, the modified retinoid compounds may be present in a pharmaceutical composition to treat and/or prevent the previously mentioned diseases and disorders in a pharmaceutically effective amount. For example, in a topical formulation, the modified retinoid compounds may be present in an amount of from about 0.01 mg/gm to about 100 mg/gm of the composition. However, the modified retinoid compounds may be administered topically, transdermally, orally or parenterally, and typical oral dosages are from about 0.5 mg/day to about 5 g/day. The proportion of each of the compounds in the composition is dependent upon the particular disease state being addressed and the degree of activity desired. In all cases, effective amounts of the compound should be used. In practice, the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. In general, either a single daily dose or divided daily dosages may be employed, as is well known in the art.

For treatment and/or prophylaxis purposes, the compounds of this invention may be formulated for pharmaceutical applications as a solution in innocuous solvents, or as an emulsion, suspension or dispersion in suitable oils, solvents or carriers, or as creams, lotions, ointments, topical patches, pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents. The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications.

Compositions for use in the above-mentioned treatment and prophylactic uses comprise an effective amount of one or more modified retinoid compound as defined by the above formula as the active ingredient, and a suitable carrier. An effective amount of such compounds for use in oral formulations in accordance with this invention is from about 0.01 mg to about 100 mg per gm of composition. However, the active ingredients may be administered topically, transdermally, orally or parenterally, and typical oral dosages are from about 0.5 mg/day to about 5 g/day.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

Inhalation of powder, self-propelling or spray formulations, dispensed with a spray can, a nebulizer or an atomizer can also be used. The formulations, when dispensed, preferably have a particle size in the range of 10 to 100 μg.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:
1. A retinoid ester having the formula

where R is a retinoyl and $R^1$ is a highly sterically hindered functional group comprising a cholesterol structure having the formula

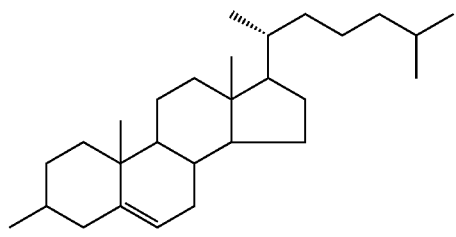

2. The retinoid ester of claim 1 wherein R is a retinoyl of all-trans-retinoic acid.

3. The retinoid ester of claim 1 wherein R is a retinoyl of a retinoid selected from the group consisting of
all-trans-retinoic acid;
9-cis-retinoic acid;
11-cis-retinoic acid;
13-cis-retinoic acid;
9,13-di-cis-retinoic acid;
TTNPB;
TTNN;
TTAB;
UAB8;
AM80;
AM580;
AM555S;
AGN 193836;
AGN 190299;
CD 2019;
CD 417;

R$_o$ 48-2249;
R$_o$ 44-4753;
R$_o$ 10-9359;
SR 11254;
BMS 185354;
AGN 190299;
CD 437 (AHPN);
SR 11247;
SR 11217;
SR 11237;
AGN 191701;
LDG 100268;
LDG 100568;
LGD 100754;
R$_o$ 25-7386;
BMS 188970;
SR 11004; and
SR 11203.

4. A retinoid ester having the formula

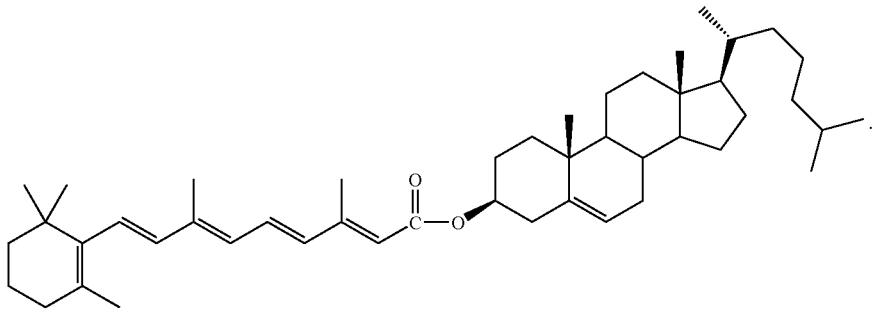

5. A pharmaceutical composition comprising a retinoid ester as set forth in claim 1 together with a pharmaceutically acceptable excipient.

6. The composition of claim 5 having from about 0.01 mg to about 100 mg of said retinoid ester per gram of the composition.

7. A pharmaceutical composition comprising a retinoid ester having the formula

8. The composition of claim 7 having from about 0.01 mg to about 100 mg of said retinoid ester per gram of the composition.

9. A method of treating psoriasis comprising administering to a patient with psoriasis an effective amount of a retinoid ester as set forth in claim 1.

10. The method of claim 9 wherein the retinoid ester is administered orally, parenterally, transdermally or topically.

11. The method of claim 9 wherein the retinoid ester is administered in a dosage of from about 5 mg to about 5 g per day.

12. The method of claim 9 wherein the retinoid ester has the formula

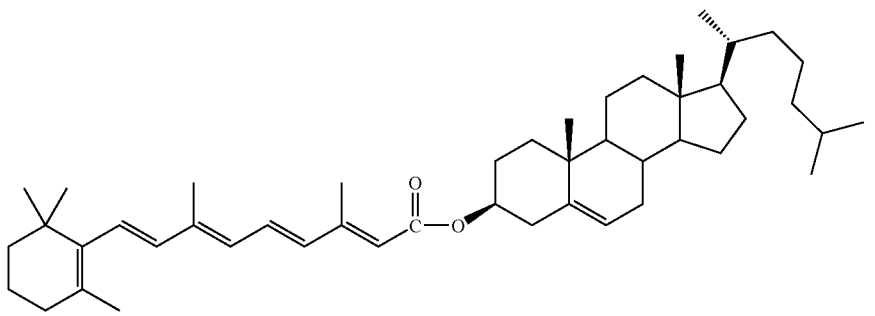

together with a pharmaceutically acceptable excipient.

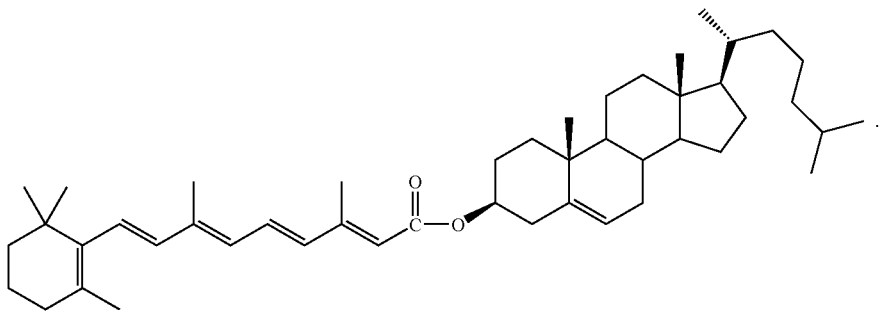

13. A method of treating acne comprising administering to a patient with acne an effective amount of a retinoid ester as set forth in claim 1.

14. The method of claim 13 wherein the retinoid ester is administered orally, parenterally, transdermally or topically.

15. The method of claim 13 wherein the retinoid ester is administered in a dosage of from about 5 mg to about 5 g per day.

16. The method of claim 13 wherein the retinoid ester has the formula

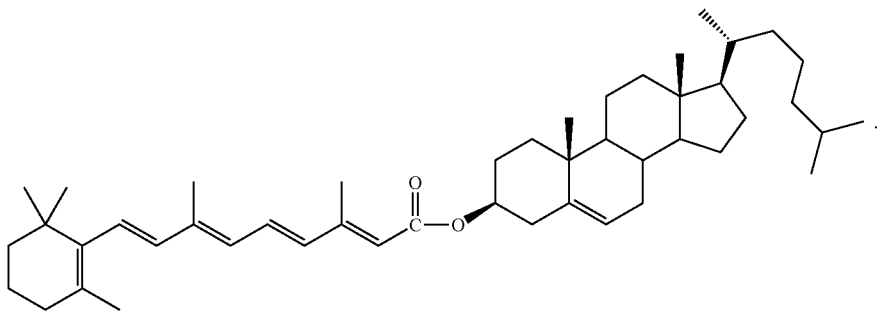

17. A method of treating skin conditions selected from the group consisting of lack of skin firmness, wrinkles, lack of dermal hydration and insufficient sebum secretion which comprises administering to a patient with one of said skin conditions an effective amount of a retinoid ester as set forth in claim 1.

18. The method of claim 17 wherein the retinoid ester is administered orally, parenterally, transdermally or topically.

19. The method of claim 17 wherein the retinoid ester is administered in a dosage of from about 5 mg to about 5 g per day.

20. The method of claim 17 wherein the retinoid ester has the formula

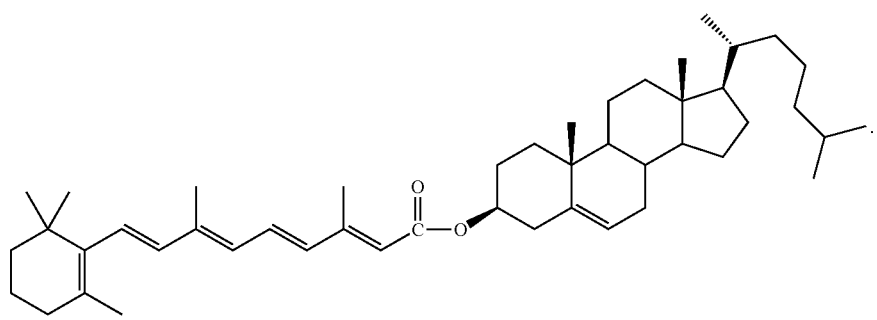

21. A method of treating a disease selected from the group consisting of skin cancer, leukemia, colon cancer, breast cancer, prostate cancer, ovarian cancer, and lung cancer comprising administering to a patient with said disease an effective amount of a retinoid ester as set forth in claim 1.

22. The method of claim 21 wherein the retinoid ester is administered orally, parenterally, transdermally or topically.

23. The method of claim 21 wherein the retinoid ester is administered in a dosage of from about 5 mg to about 5 g per day.

24. A method of treating a disease selected from the group consisting of dermatitis, eczema and keratosis comprising administering to a patient with said disease an effective amount of a retinoid ester as set forth in claim 1.

25. The method of claim 24 wherein the retinoid ester is administered orally, parenterally, transdermally or topically.

26. The method of claim 24 wherein the retinoid ester is administered in a dosage of from about 5 mg to about 5 g per day.

* * * * *